United States Patent [19]
Vetter et al.

[11] Patent Number: 5,851,838
[45] Date of Patent: Dec. 22, 1998

[54] DIAGNOSTIC TEST CARRIER WITH A CAPILLARY GAP

[75] Inventors: Peter Vetter, Schifferstadt; Heinz Macho, Fürth; Peter Vogel, Hemsbach; Michael Fritz, Biblis, all of Germany

[73] Assignee: Boehringer Mannheim GmbH, Mannheim, Germany

[21] Appl. No.: 897,509

[22] Filed: Jul. 21, 1997

[30] Foreign Application Priority Data

Jul. 23, 1996 [DE] Germany ............... 196 29 654.4

[51] Int. Cl.$^6$ ..................................................... G01N 33/48
[52] U.S. Cl. ............................ 436/170; 436/177; 422/58
[58] Field of Search .............................. 422/56, 58, 61, 422/101, 102, 100; 436/68, 86, 169, 170, 177

[56] References Cited

U.S. PATENT DOCUMENTS

| | | | |
|---|---|---|---|
| 2,785,057 | 3/1957 | Schwab et al. | 422/58 |
| 3,509,872 | 5/1970 | Truhan | 422/58 |
| 4,258,001 | 3/1981 | Pierce et al. | 422/56 |
| 4,312,834 | 1/1982 | Vogel et al. | 422/56 |
| 4,477,575 | 10/1984 | Vogel et al. | 436/170 |
| 4,647,430 | 3/1987 | Zweig | 422/58 |
| 4,816,224 | 3/1989 | Vogel et al. | 422/58 |
| 5,096,836 | 3/1992 | Macho et al. | 436/169 |

FOREIGN PATENT DOCUMENTS 0 348 006  12/1989  European Pat. Off. .

*Primary Examiner*—Lyle A. Alexander
*Attorney, Agent, or Firm*—Nikaido, Marmelstein, Murray & Oram LLP

[57] ABSTRACT

The invention concerns a diagnostic test carrier (1) containing a supporting layer (2) with a detection layer (3) arranged thereon containing reagents required for the determination of an analyte in a liquid sample and an inert layer (4) covering the detection layer (3) wherein the inert layer (4) is arranged at such a distance (5) from the detection layer to enable a capillary active liquid transport between the detection layer and inert layer (3,4), characterized in that the inert layer (4) extends beyond the detection layer and wherein the area (10) that extends beyond the detection layer is attached to the supporting layer (2) in such a way that a continuous capillary active liquid transport between the inert layer and detection layer (4,3) and between the inert layer and supporting layer (4,2) is possible and in addition the inert layer (4) contains several holes (7) in the area of the detection layer (3) through which the sample to be examined and the components contained therein can be applied to the detection layer (3) as well as its use for the determination of an analyte in a liquid.

29 Claims, 2 Drawing Sheets

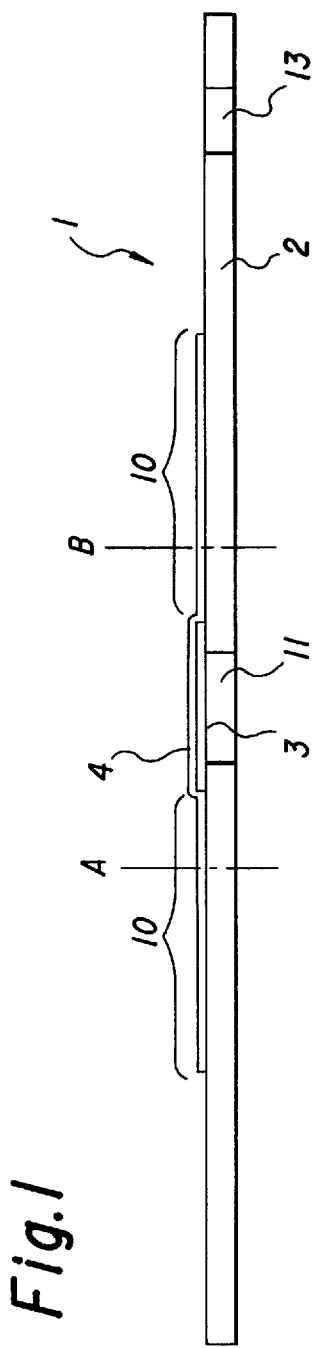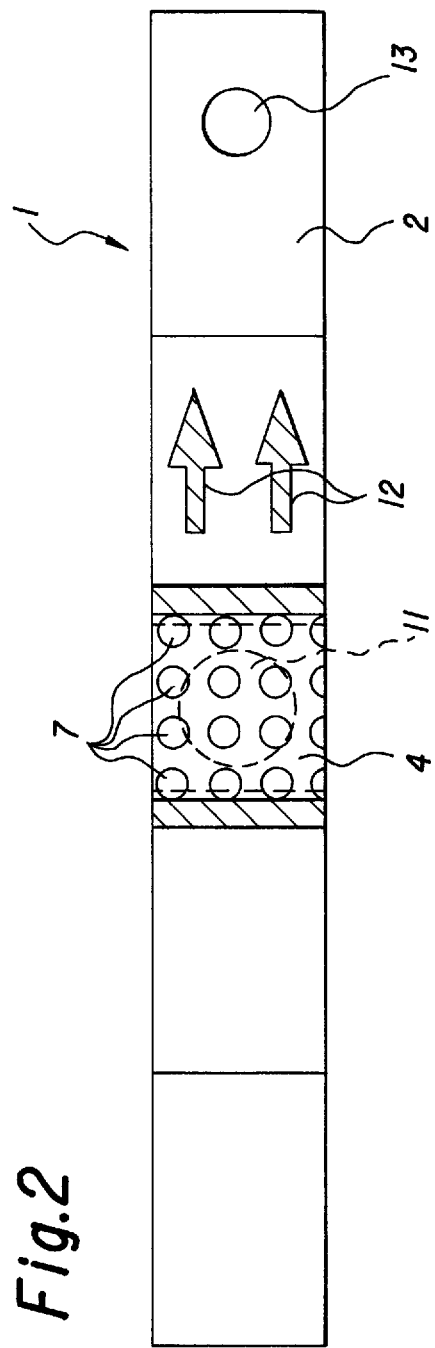

DIAGNOSTIC TEST CARRIER WITH A CAPILLARY GAP

The invention concerns a diagnostic test carrier containing a supporting layer with a detection layer arranged thereon containing reagents required for the determination of an analyte in a liquid sample and an inert layer covering the detection layer wherein the inert layer is arranged at such a distance from the detection layer that a gap is present between the detection layer and the inert layer which enables a capillary active liquid transport. In addition the invention also concerns the use of such a diagnostic test carrier to determine an analyte in a liquid.

So-called carrier-bound tests are often used for the qualitative or quantitative analytical determination of components of body fluids in particular of blood. In these the reagents are embedded in appropriate layers of a solid test carrier which is contacted with the sample. The reaction of the liquid sample and reagents leads to a detectable signal in particular a colour change which can be analysed visually or with the aid of an instrument, usually by reflection photometry.

Test carriers are frequently in the form of test strips which are composed essentially of an elongate supporting layer made of plastic material and detection layers applied thereto as test zones. However, test carriers are also known which are shaped as quadratic or rectangular slides.

Test carriers of the type referred to above are known for example from EP-A-0 348 006. In this case it is intended above all to achieve a uniform distribution of sample liquid over the test zone which is a part of the detection layer containing the reagents required to determine the analyte. The object is achieved according to the information stated in the European Patent Application by the fact that a capillary gap is located above the test zone. This is filled with liquid after sample application and when measuring the test (see for example page 6, lines 3 to 6 or FIG. 5). Hence the capillary gap and the absorption volume of the test zone define the sample volume which is taken up by the test carrier and is examined there. A major disadvantage of this test carrier of the state of the art is that during the time which is required to carry out the determination reaction and during which the analyte is consumed, analyte continuously rediffuses out of the surrounding liquid and thus falsifies the result.

A diagnostic test carrier is also known from EP-A-0 297 389 in which a liquid transport zone and a detection zone are arranged next to one another on a supporting layer which are linked together by a capillary gap. The construction of the test carrier is such that when the sample application is undosed and hence the required excess sample liquid is present, the entire capillary gap is filled with liquid. Also in this case the analyte which is consumed in the detection zone by the detection reaction is then replaced by analyte which rediffuises from the surrounding liquid and can positively falsify the result.

Therefore the object of the present invention is to provide a diagnostic test carrier for the determination of an analyte in a liquid on which an undosed amount of sample liquid can be applied and which does not lead to false-positive results due to rediffusion of analyte from the surrounding liquid when there is an excess of sample liquid.

This object is achieved by the invention characterized in more detail by the patent claims.

The subject matter of the invention is namely a diagnostic test carrier which contains a detection layer on a supporting layer for the determination of an analyte in a liquid sample. The detection layer contains the necessary reagents for the detection of the analyte. The detection layer is covered by an inert layer in such a way that a gap is formed between the inert layer and the detection layer that is of an adequate size to enable capillary active liquid transport between the detection layer and the inert layer. The inert layer is larger than the detection layer and therefore extends beyond the latter. In the area which protrudes beyond the detection layer the inert layer is attached to the supporting layer in such a way that there is also a gap here between the supporting layer and the inert layer which enables a capillary active liquid transport between these layers. Since according to the invention the inert layer is arranged such that there is only a small distance between it and the layer below over the entire diagnostic test carrier, a continuous capillary active liquid transport is possible between the inert layer and detection layer and between the inert layer and supporting layer. The inert layer has several holes in the area of the detection layer through which the sample to be examined and components contained therein can be applied to the detection layer.

Materials which come into consideration for the supporting layer of the diagnostic test carrier according to the invention are those which do not absorb the liquids to be examined. These are so-called non-absorptive materials, plastic foils such as for example polyester foils being particularly preferred.

In contrast it is necessary to use materials for the detection layer which are able to absorb the liquid to be examined together with the components contained therein. These are so-called absorptive materials such as papers, fleeces, fabrics, knitted fabrics or porous plastic materials which can be used as layer materials. The materials which come into consideration for the detection layer must of course also be able to carry reagents that are required for the detection of the analyte to be determined. In the simplest case all the reagents required to detect the analyte are located on one layer. However, cases are also conceivable in which it is more advantageous to distribute the reagents over several absorptive material layers which are then arranged one above the other such that their whole surfaces are in contact. The term "detection layer" used in the following is intended to encompass those cases in which the reagents are located either only in or on one layer or in two or even more layers arranged as described above. Preferred materials for the detection layer are papers or porous plastic materials such as membranes. Asymmetric porous membranes are particularly preferred which are arranged advantageously such that the sample liquid to be examined is applied to the large-pored side of the membrane and the analyte is determined on the fine-pored side of the membrane.

Polyamide, polyvinylidene difluoride, polyethersulfone or polysulfone membranes are quite especially preferred as porous membrane materials. Polyamide 66 membranes are in particular excellently suitable for the test carrier according to the invention. The reagents for the determination of the analyte to be detected have usually been introduced by impregnation into the aforementioned materials. However, so-called open films also come into consideration for the detection layer as described for example in EP-B-0 016 387. For this an aqueous dispersion of film-forming organic plastic solids are added as fine insoluble organic or inorganic particles and the reagents required for the detection reaction are additionally added. Suitable film formers are preferably organic plastics such as polyvinyl esters, polyvinyl acetates, polyacrylic esters, polymethacrylic acid, polyacrylamides, polyamides, polystyrene, mixed polymers such as of butadiene and styrene or of maleic acid esters and vinyl acetate or other film forming natural and synthetic organic polymers as well as mixtures of the same in the form of aqueous dispersions. The dispersions can be distributed onto a base to form a uniform layer which yields a water-resistant film after drying. The dry films have a thickness of 10 $\mu$m to 500 $\mu$m preferably of 30 to 200 $\mu$m. The film can be used together with the base as a carrier or can be mounted on another carrier for the detection reaction. Although the reagents required for the detection reaction are normally added to the dispersion used to produce the open films, it may also be advantageous to impregnate the film that is formed with the reagents after it has been manufactured. It is also possible to pre-impregnate the fillers with the reagents. Which reagents can be used to determine a particular analyte are known to a person skilled in the art. This does not need to be elucidated here in more detail.

In addition the detection layer can also contain a layer which is able to separate plasma or serum from whole blood such as for example a glass fibre fleece like that which is known from EP-B-0 045 476. One or several such separation layers can lie on top of one or several layers which carry detection reagents. The term "detection layer" also includes such a structure.

Thin essentially water-impermeable materials come into consideration for the inert layer of the diagnostic test carrier according to the invention. Plastic foils have proven to be particularly well-suited for this. In order that the sample liquid to be examined can pass through the inert layer to reach the detection layer, the inert layer contains holes in the area of the detection layer. These holes can have all possible shapes. They can for example be rectangular, quadratic, polygonal or round. Round holes have proven to be preferable for technical manufacturing reasons. The holes can be arranged uniformly but they can, however, also be distributed purely statistically. The holes can be of the same size or of a different size. For manufacturing reasons it has proven to be technically preferable that the holes are of the same size and are arranged in a regular pattern. It is quite especially preferable that the holes are placed in the inert foil in uniformly arranged parallel rows. The inert layer has a raster of holes in the area of the detection layer whereby the area of the holes constitutes 30 to 80% preferably 40 to 70% of the detection layer area. In a quite especially preferred embodiment the smallest distance between the holes corresponds to the hole diameter. The size of the hole i.e. the largest hole diameter is about 0.5 to 2 mm preferably 0.6 to 1.5 mm.

The characteristic capillary liquid transport of the diagnostic test carrier according to the invention between the inert layer and the detection layer as well as between the inert layer and supporting layer is achieved by arranging the respective layers on top of one another with a small distance between them. This distance between the inert layer and the supporting layer is preferably less than the distance between the inert layer and the detection layer. The magnitude of this distance is approximately between 0.02 and 1.2 mm preferably 0.4–1 mm. In order to maintain a particular distance between the respective layers over the entire width and length of the area of the diagnostic test carrier which comes into consideration, it has proven to be advantageous to place spacers between the layers. Discrete hot-melt adhesive areas are particularly preferred for this as they are for example known from the European Patent Application 0 297 389. Products that are commercially available can be used as hot-melt adhesives for example based on ethylene vinylacetate copolymers, polyesters or polyamides. The areas of hot-melt adhesive that serve as spacers can have different shapes. In any case they have to be formed in such a way that sufficiently large gaps remain so that liquid transport between them is possible. They preferably cover between 10 and 70% particularly preferably between 15 and 50% of the entire area between the respective layers to be kept at a distance from one another. It has proven to be particularly advantageous when the hot-melt adhesive in the form of particles i.e. for example in the form of round, quadratic or polygonal spots serves as spacers. In a particularly preferred embodiment of the diagnostic test carrier the hot-melt adhesive areas are attached to the inert layer. They only rest on the detection layer and are also not attached there. However, outside the detection layer the hot-melt adhesive areas are attached to the inert layer as well as to the supporting layer. In order to ensure a gap distance which is as regular as possible between the two layers that are linked by means of the hot-melt adhesive areas, the hot-melt adhesive areas are preferably of the same size and dispersed regularly over the entire area of linkage. The hot-melt adhesive particles preferably have an average base area between 0.03 and 5.0 mm$^2$. The upper limit is preferably 0.1 mm$^2$.

In order to determine the analyte to be detected in the sample liquid the detection layer is visible through the supporting layer in the diagnostic test carrier according to the invention. This can be achieved by a transparent supporting layer. However, it is also possible that the supporting layer has a hole which is covered by the detection layer. The detection layer is then visible through the hole. In a preferred embodiment of the diagnostic test carrier according to the invention a hole is located in the supporting layer underneath the detection layer through which the detection layer can be observed. The hole has a slightly smaller diameter than the smallest linear extension of the detection layer so that the detection layer rests on the supporting layer outside the hole and can be attached thereto. It has for example proven to be advantageous when the detection layer is attached to the supporting layer by means of a thin hot-melt adhesive layer.

The inert foil is provided with zones of hot-melt adhesive before it is applied to the detection layer and supporting layer. The hot-melt adhesive can for example be applied by screen printing. Other methods are known to a person skilled in the art for example from the European Patent Application 0 297 389. A process is described in this application in which the hot-melt adhesive is pressed through the holes of a mesh by means of a nozzle with a broad slit in which case the shape of the particles of hot-melt adhesive formed in this process is determined by the shape of the holes of the mesh. Since when the hot-melt adhesive is applied to the inert foil it is still so hot that it touches the inert layer in a melted state it adheres firmly to it when it cools down.

After the zones of hot-melt adhesive have been applied, holes can be made in the inert layer which are located in the area of the detection layer in the later diagnostic test carrier according to the invention. The inert layer prepared in this manner is placed on the supporting layer and the detection layer which is located thereon. The areas of hot-melt adhesive which are located outside the detection layer are subsequently heated up again so that the areas at least melt superficially. The inert layer is attached to the supporting layer by pressing the inert layer onto the supporting layer outside the area of the detection layer. In this process the pressure must not be so high that there is no longer a gap between the inert layer and the supporting layer. In this case a capillary active liquid transport would no longer be possible.

A preferred embodiment of the diagnostic test carrier according to the invention and details of this test carrier are shown in FIGS. 1–5.

BRIEF DESCRIPTION OF THE DRAWINGS

FIG. 1 shows a cross-section through a preferred diagnostic test carrier according to the invention.

FIG. 2 shows a top view of the diagnostic test carrier according to the invention shown in cross-section in FIG. 1.

Figure 3:
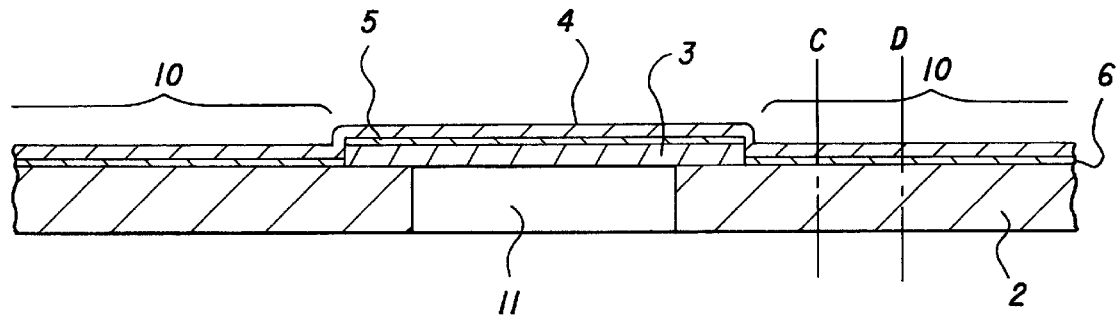
FIG. 3 shows an enlarged section of the cross-section shown in FIG. 1 between A and B.

The reference numerals used in the figures denote:
1. diagnostic test carrier
2. supporting layer
3. detection layer
4. inert layer
5. gap between detection layer and inert layer
6. gap between supporting layer and inert layer
7. holes in the inert layer in the area of the detection layer
8. spacers
9. intermediate space between spacers
10. area of the inert layer which extends beyond the detection layer
11. hole in the supporting layer under the detection layer
12. direction arrows on the inert layer
13. positioning hole The cross-section shown in FIG. 1 through a diagnostic test carrier according to the invention (1) shows a supporting layer (2) with the detection layer (3) and the inert layer (4) covering the detection layer (3) which is attached to the supporting layer (2) in the area (10) which extends beyond the detection layer (3). A hole (11) in the supporting layer (2) is located under the detection layer (3) through which the detection layer (3) is visible. The positioning hole (13) serves to hold the test strip at an exactly predetermined position of the instrument in the case of a measurement by an apparatus for example by reflection photometry. This can for example be achieved by a pin which extends into the positioning hole (13) and thus holds the test strip (1) at a predetermined position.

The top view shown in FIG. 2 of the diagnostic test carrier (1) according to the invention shows holes (7) which are located in the inert layer (4) in the area of the detection layer (3). The hole (11) in the supporting layer (2) is shown as a dotted line in this figure. The direction arrows (12) on the inert layer (4) outside the area of the detection layer (3) show the user, in the case that an instrument is used for determination in an apparatus, in which direction the test strip should be inserted into the instrument. As already stated above the positioning hole (13) at the end of the test carrier (1) then helps to position it in the instrument.

The enlarged section shown in FIG. 3 of the cross-section shown in FIG. 1 between A and B shows the distance (5) between the inert layer (4) and the detection layer (3) on the one hand and the distance (6) between the inert layer (4) and supporting layer (2) on the other hand. Also in the area of the edges of the detection layer (3) the inert layer (4) does not fit so tightly that a capillary active liquid transport would not be possible from the area of the detection layer (4) into the area (10) of the inert layer (4) which extends beyond the detection layer (3).

Figure 4:
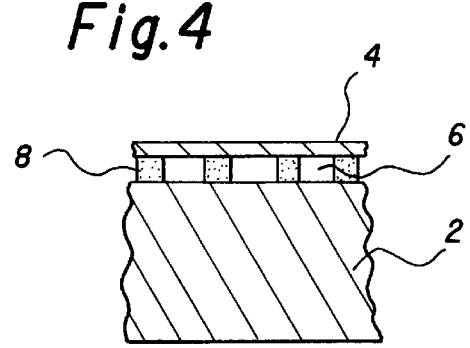
FIG. 4 shows a detail of the cross-section shown in FIG. 3 between C and D.
Figure 5:
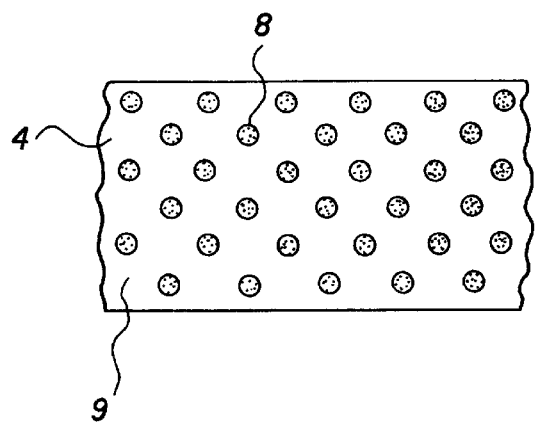
FIG. 5 shows a top view of a part of an inert layer with spacers as they face towards the supporting layer in the diagnostic test carrier according to the invention.

The detail shown in FIG. 4 of the cross-section shown in FIG. 3 between C and D shows the spacers (8) between the inert layer (4) and the supporting layer (2) which set a certain distance (6) between the supporting layer (2) and inert layer (4). A possible arrangement of the spacers (8) on the inert layer (4) is shown in FIG. 5. In this case the spacers are arranged diagonally to the inert layer (4) in parallel rows. Of course other arrangements are also possible provided a uniform distance between the respective layers can be guaranteed and the intermediate space (9) between the spacers is large enough that a capillary active liquid transport can take place between the layers.

A diagnostic test carrier according to the invention can be used very advantageously to determine an analyte in a liquid. For this the liquid to be examined which is advantageously in particular a body fluid such as blood, plasma, serum or urine is applied to the holes of the inert layer. Liquid reaches the absorptive detection layer through the holes. In addition liquid also passes through the holes into the intermediate space between the inert layer and detection layer and is dispersed uniformly due to the capillary forces which act there. In this way an overall very advantageous spreading effect takes place so that the detection layer as a whole can absorb liquid steadily and uniformly. Excess liquid which can no longer be absorbed by the detection layer is sucked away from the detection layer through the space between the inert layer and supporting layer. This ensures that the suction volume of the detection layer determines the volume of sample liquid which becomes available for the analysis. During the detection reaction and the concomitant consumption of analyte in the liquid located in the detection layer the transport of excess liquid away from the detection layer prevents further analyte from reaching the detection layer and positively falsifying the result. The detection layer can be observed directly through the supporting layer. A colour transition or colour change which for example occurs when the analyte to be determined is present in the sample liquid can thus be observed visually or by an instrument. Due to the fact that the volume of the sample liquid to be examined can be predetermined as a result of the dimensions and character of the material of the detection layer and that excess liquid is sucked away after the detection layer becomes saturated and thus interfering effects are avoided, the diagnostic test carrier according to the invention can be used to carry out not only a qualitative but also a quantitative determination of analytes without having to dose the sample liquid to be examined. Since excess liquid is sucked away from the detection layer into the space between the inert layer and supporting layer hygienic aspects are also taken into account. A dripping of liquid from the test carrier or contact of liquid for example with parts of an instrument into which the test carrier is placed for instrumental evaluation is reliably avoided. This is a very important aspect in the examination of blood or samples derived from blood such as plasma or serum.

Due to the fact that the test carrier according to the invention is only composed of a few components the test carrier can be manufactured particularly simply and cost-effectively.

EXAMPLE 1

Test Carrier for the Determination of Haemoglobin in Blood

A test carrier according to FIG. 1 is manufactured by soaking an asymmetric porous membrane (BTS 65, Memtec America Corp., Timonium Md., USA) with a width of 28 cm as a detection layer (3) in a solution of 1% by weight sodium dodecylsulfate and 0.7 mmol/l potassium hexacyanoferrate (III) in 0.1N phosphate buffer pH 7. The membrane loaded with liquid is dried for 30 minutes at 50° C. The dry membrane is cut into 6 mm wide strips and placed on a 350 μm thick, 48 mm wide polyester foil (Melinex 329 of the ICI Company) as a supporting layer (2). This foil contains 2 rows of holes (11 and 13). The holes in the first row have a diameter of 4 mm. They are at a distance of 2.4 mm from one another and the centre of the holes is in each case at a distance of 25 mm from the right edge of the foil. In the second row of holes which are arranged parallel to the first row the holes have a diameter of 2.5 mm. They are at a distance of 3.5 mm from one another and the centre of the holes is in each case at a distance of 4 mm from the right edge of the foil. The membrane is positioned such that its fine-pored side comes to lie over the first row of the holes (11) of 4 mm diameter.

A 50 μm thick and 24 mm wide Hostaphan® FN50 foil (Hoechst AG) as an inert layer (4) which is coated with a raster application of hot-melt adhesive spots (Elvax 410 from the DuPont Company) (8) is provided with holes (7) of a diameter of 1.5 mm in the middle over a width of 5.5 mm using a rotary punch. The foil with the hot-melt adhesive spots is positioned on the polyester foil such that the punched area is located over the matrix and the unpunched areas (10) are left and right of the membrane. A hot roller with a gap set to 0.7 mm fixes the Hostaphan® foil onto the polyester foil at a temperature between 90° and 100° C. so that a capillary gap (9) remains between the two foils. Subsequently the tape obtained in this manner is cut into 6 mm wide test carriers of FIG. 1. Ca. 10μl whole blood is applied to the holes in the inert layer (4). The test strip is examined after ca. 45 seconds through the hole (11)) under the membrane in the supporting layer. A uniform dark coloration is observed which correlates with the haemoglobin content of blood.

What is claimed is:

1. A diagnostic test carrier, comprising
a supporting layer;
a detection layer arranged on the supporting layer, said detection layer carrying reagents for the detection of an analyte in a liquid sample; and
an inert layer covering and extending beyond the detection layer onto the supporting layer, to which supporting layer the inert layer is attached,
wherein the inert layer contains at least one hole in the area of the inert layer covering the detection layer, through which at least one hole the liquid sample can be applied to the detection layer,
wherein the inert layer is spaced from the detection layer at a distance which allows a capillary liquid transport between the detection layer and the inert layer,
and wherein the inert layer is spaced from the supporting layer at a distance such that a capillary liquid transport between the inert layer and the supporting layer is also possible.

2. The diagnostic test carrier according to claim 1, wherein the supporting layer comprises a material which is essentially non-absorbent.

3. The diagnostic test carrier according to claim 2, wherein the supporting layer comprises a polyester foil.

4. The diagnostic test carrier according to claim 1, wherein the detection layer comprises a material that can absorb liquid.

5. The diagnostic test carrier according to claim 4, wherein the detection layer comprises a porous membrane.

6. The diagnostic test carrier according to claim 1, wherein the liquid sample is a body fluid.

7. The diagnostic test carrier according to claim 6, wherein the liquid sample is whole blood and the detection layer further comprises a layer which is able to separate plasma or serum from the whole blood.

8. The diagnostic test carrier according to claim 1, wherein the inert layer comprises a material which is essentially non-absorbent.

9. The diagnostic test carrier according to claim 1, wherein the inert layer has a plurality of holes exposing 30% to 80% of the surface area of the detection layer.

10. The diagnostic test carrier according to claim 1, wherein the inert layer has a plurality of holes exposing 40% to 70% of the surface area of the detection layer.

11. The diagnostic test carrier according to claim 1, wherein the distance between the inert layer and the supporting layer is less than the distance between the inert layer and the detection layer.

12. The diagnostic test carrier according to claim 1, wherein the distance between the inert layer and the supporting layer is between about 0.02 mm and about 1.2 mm.

13. The diagnostic test carrier according to claim 1, wherein the distance between the inert layer and the supporting layer is between about 0.4 mm and about 1 mm.

14. The diagnostic test carrier according to claim 1, wherein the distance between the inert layer and the detection layer is between about 0.02 mm and about 1.2 mm.

15. The diagnostic test carrier according to claim 1, wherein the distance between the inert layer and the detection layer is between about 0.4 mm and about 1 mm.

16. The diagnostic test carrier according to claim 1, wherein a plurality of spacers define the distance between the detection layer and the inert layer, and between the supporting layer and the inert layer, said spacers being distanced from one another such that capillary liquid transport is possible between the spacers and between the layers separated by the spacers.

17. The diagnostic test carrier according to claim 16, wherein the spacers are discrete hot-melt adhesive zones.

18. The diagnostic test carrier according to claim 17, wherein the hot-melt adhesive zones are attached to the inert layer, and the hot-melt adhesive zones are substantially unattached to the detection layer.

19. The diagnostic test carrier according to claim 16, wherein the spacers cover between 10% and 70% of the area between the spaced apart respective layers.

20. The diagnostic test carrier according to claim 16, wherein the spacers cover between 15% and 50% of the area between the respective layers to be kept at a distance from one another.

21. The diagnostic test carrier according to claim 1, wherein the detection layer has two sides and is visible from at least one side.

22. The diagnostic test carrier according to claim 21, wherein the supporting layer is substantially transparent to permit the detection layer to be visible therethrough.

23. The diagnostic test carrier according to claim 21, wherein the supporting layer has at least one hole, through which the detection layer is visible, and wherein the hole is smaller than the detection layer such that the detection layer contacts at least a portion of an area of the supporting layer surrounding the hole.

24. The diagnostic test carrier according to claim 1, wherein the detection layer has reagents embedded therein for the detection of an analyte in a liquid.

25. A method of using a diagnostic test carrier comprising a supporting layer; a detection layer arranged on the supporting layer, said detection layer carrying reagents, and an inert layer covering and extending beyond the detection layer onto the supporting layer, to which said inert layer is attached, wherein the inert layer contains at least one hole in the area of the inert layer covering the detection layer, through which at least one hole a liquid sample containing analytes to be detected is applied to the detection layer, wherein the inert layer is spaced from the detection layer at a distance which allows a capillary liquid transport between the detection layer and the inert layer, and wherein the inert layer is spaced from the supporting layer at a distance such that a capillary liquid transport between the inert layer and the supporting layer is also possible, comprising passing the liquid sample through the inert layer to the diagnostic layer, with removal of excess liquid through capillary action, to produce a detectable signal in the diagnostic layer from reaction of the liquid sample with the reagents in the diagnostic layer; and detecting the signal.

26. The method of using a diagnostic test carrier according to claim 25, wherein the detectable signal is a color change signal.

27. The method of using a diagnostic test carrier according to claim 25, wherein the liquid sample is blood.

28. The method of using a diagnostic test carrier according to claim 25, wherein the detection layer has reagents embedded therein.

29. A diagnostic test carrier, comprising a supporting layer;

a detection layer means, arranged on the supporting layer, for determining an analyte in a liquid sample; and an inert layer means, spaced on the supporting layer and on the detection layer means, for holding the test carrier components together, for allowing transport therethrough from the exterior of the test carrier to the detection layer, and for defining a capillary space between the inert layer means and the detection layer means and between the inert layer means and the supporting layer, wherein excess liquid is removed through the capillary space by capillary action.

* * * * *